United States Patent [19]

Kemp et al.

[11] Patent Number: 5,119,315
[45] Date of Patent: Jun. 2, 1992

[54] METHOD OF CORRELATING A RECORD OF SAMPLE DATA WITH A RECORD OF REFERENCE DATA

[75] Inventors: Marwin K. Kemp, Tulsa; William A. Cooper, Jr., Claremore; David L. Dolcater, Tulsa, all of Okla.

[73] Assignee: Amoco Corporation, Chicago, Ill.

[21] Appl. No.: 345,325

[22] Filed: Apr. 28, 1989

[51] Int. Cl.$^5$ .................... G06F 15/20; G06F 15/74
[52] U.S. Cl. ................................ 364/498; 364/421; 364/487
[58] Field of Search .................... 364/496-98, 364/422, 421, 571.01, 571.05, 579, 481, 487; 324/76 R, 77 G, 79 R; 73/23.21, 61.1 C; 250/269

[56] References Cited

U.S. PATENT DOCUMENTS

| | | | |
|---|---|---|---|
| 3,797,300 | 3/1974 | Sato | 73/23.1 |
| 3,898,837 | 8/1975 | Boege | 73/23.1 |
| 4,008,388 | 2/1977 | McLafferty et al. | 364/498 |
| 4,314,343 | 2/1982 | Tomlinson | 364/498 |
| 4,353,242 | 10/1982 | Harris et al. | 73/23.1 |
| 4,546,643 | 10/1985 | Bonneyrat et al. | 73/61.1 C |
| 4,573,354 | 3/1986 | Voorhees et al. | 364/498 |
| 4,574,354 | 3/1986 | Mihalik et al. | 364/487 |
| 4,578,578 | 3/1986 | Lin et al. | 250/269 |
| 4,583,183 | 4/1986 | Winiecki et al. | 364/498 |
| 4,835,708 | 5/1989 | Frans | 364/498 |
| 4,847,793 | 7/1989 | Cygnarowicz et al. | 364/571.05 |
| 4,916,645 | 4/1990 | Wuest et al. | 364/571.01 |

OTHER PUBLICATIONS

Pino et al., "Application of Pyrolysis/Gas Chromatography/Pattern Recognition to the Detection of Cystic Fibrosis Heterozygotes", *Anal. Chem.* vol. 57, No. 1, Jan. 1985, pp. 295-302.

Parrish et al., "Computer-Enhanced High-Resolution Gas Chromatography for the Discriminative Analysis of Tobacco Smoke", *Anal. Chem.*, vol. 53, No. 6, May, 1981, pp. 826-831.

*Primary Examiner*—Kevin J. Teska
*Attorney, Agent, or Firm*—Marcy M. Lyles

[57] ABSTRACT

A method of aligning a time record of sample data, such as a mass chromatogram of an unknown substance, with a time record of reference data, such as a mass chromatogram of a known substance. A coarse time-related alignment between the sample data and the reference data is produced independently of any similarities and differences between the sample data and the reference data. A determination is made of which, if any, distinguishing coarsely aligned sample data are within a predetermined time-related tolerance of any distinguishing reference data. For each distinguishing sample data which is within a predetermined time-related tolerance of a respective distinguishing reference date, a fine time-related alignment is produced between the respective sample data and its respective reference data. The respective sample data is then recorded with substantially the same time designation as the respective reference data.

5 Claims, 13 Drawing Sheets

METHOD OF CORRELATING A RECORD OF SAMPLE DATA WITH A RECORD OF REFERENCE DATA

BACKGROUND OF THE INVENTION

1. Field of the Invention

This invention relates to a method of aligning a record of sample data with a record of reference data. In a particular aspect, the present invention relates to a method of aligning a time record of sample data with a time record of reference data. Another aspect of the invention relates to a method of aligning the signals of a sample mass chromatogram with the signals of a reference mass chromatogram, and more particularly to a method of aligning signals of a sample chromatogram to signals of a primary standard chromatogram using a secondary standard chromatogram which includes signals corresponding to signals of the primary standard chromatogram but located at different times therefrom. Another aspect of the present invention relates to a method of analyzing a sample substance using mass chromatograms in which constituents of substances are designated by signals aligned to time designations, and more specifically it relates to a method of comparing at least two unknown hydrocarbon-bearing substances. Another aspect of the present invention includes a method of reservoir analysis for one or more subterranean fluid-containing reservoirs. Still another aspect of the present invention includes a method of aligning sample records so that the aligned sample records define a database on which a meaningful statistical analysis can be performed, wherein the sample records are gas chromatography/mass spectrometry (GC/MS) constituent peak-time records for a plurality of samples.

2. Setting of the Invention

One technique for analyzing a substance, such as crude oil or a rock extract taken from an oil well, is to process the substance through gas chromatography/mass spectrometry (GC/MS) equipment. This equipment detects the presence of different constituents or components of the substance which have, or are given, net electric charges. These electrically charged constituents may be referred to as fragments having respective mass-per-charge (m/z) values. For each constituent or fragment detected, a respective graph or collection of data, called an ion chromatogram or mass chromatogram, is produced. Each chromatogram shows intensity or quantitative data of a particular m/z fragment versus its time of detection, given as a scan number or a retention time. The intensity or quantity is a distinct or distinguishable feature or characteristic, and it is graphically represented by a peak signal. Usually, only a small portion of the total time of a chromatogram is of interest for a particular m/z profile. The region containing useful information for a given m/z is called a time window or window-of-interest.

Ideally, detection of the same m/z fragment at two different processing times would produce the same chromatogram so that direct comparisons could be made to analyze an unknown mixture relative to a known substance. Thus, for example, analyses of unknown crude oils or rock extracts could be made in the oil and gas industry, or aligned databases could be available for accurate statistical analysis. Unfortunately, data, as taken directly from GC/MS equipment, do not meet this ideal. Flow changes, procedure temperature variations, column aging, etc., contribute to later taken chromatograms typically being offset time-wise from earlier taken chromatograms. This deficiency has been known, and proposals regarding alignment or correlation of one chromatogram to another have been made. See U.S. Pat. No. 3,898,837 to Boege; J. A. Pino et al., "Application of Pyrolysis/Gas Chromatography/Pattern Recognition to the Detection of Cystic Fibrosis Heterozygotes," Analytical Chemistry, Vol. 57, No. 1, pp. 295-302 (January, 1985); M. E. Parrish et al., "Computer-Enhanced High-Resolution Gas Chromatography for the Discriminative Analysis of Tobacco Smoke," Analytical Chemistry, Vol. 53, No. 6, pp. 826-831 (May, 1981).

Because of the time offset which can result between one chromatogram and another when two are taken at substantially different times, there is the need for a method by which a mass chromatogram for an unknown sample can be aligned, preferably automatically, with a reference mass chromatogram regardless, at least initially, of differences or similarities between the two chromatograms. That is, there is the need for a method which can align two chromatograms even when they appear to be widely divergent, such as due to the peak signals of one chromatogram not being within a typical tolerance which may have been suggested in prior types of alignment or correlation techniques or such as due to the absence of one or more of the peak signals in one of the chromatograms. Satisfying these needs would be useful in providing an improved method of analyzing a sample substance using mass chromatograms and particularly a method of comparing at least two unknown hydrocarbon-bearing substances. Satisfying these needs would also be useful in implementing a method of reservoir analysis for one or more subterranean fluid-containing reservoirs and in a method of aligning sample records so that the aligned sample records define a database on which a meaningful statistical analysis can be performed.

SUMMARY OF THE INVENTION

The present invention overcomes the foregoing deficiencies and meets the above-described needs which are described with reference to chromatograms; however, the utility of the present invention is not limited to chromatograms. For accomplishing this, the present invention provides a novel and improved method of aligning a record of sample data with a record of reference data. More particular aspects of the present invention include those described hereinafter.

The present invention provides a method of aligning a time record of sample data with a time record of reference data. A coarse time-related alignment between the sample data and the reference data is produced, independently of any similarities and differences between the sample data and the reference data. A determination is made of which, if any, distinguishing coarsely aligned sample data are within a predetermined time-related tolerance of any distinguishing reference data. For each distinguishing sample data which is within a predetermined time-related tolerance of a respective distinguishing reference data, a fine time-related alignment is produced between the respective sample data and its respective reference data so that the respective sample data is then recorded with substantially the same time designation as the respective reference data.

The present invention more particularly provides a method of aligning signals of a sample mass chromatogram with signals of a reference mass chromatogram. In this method signals of the sample mass chromatogram are coarsely time-aligned with signals of the reference mass chromatogram independently of any similarities and differences between signals of the sample mass chromatogram and signals of the reference mass chromatogram so that a coarse time-aligned sample mass chromatogram is produced. For distinct signals of the coarse time-aligned sample mass chromatogram which are within a predetermined time interval of a distinct signal of the reference mass chromatogram, such signals are further time-aligned so that a fine time-aligned sample mass chromatogram is produced.

The present invention also provides a method of comparing at least two unknown hydrocarbon-bearing substances. In this method, a first analysis of a reference hydrocarbon-bearing substance is produced, wherein distinguishable characteristic signals with respective first times are designated. A second analysis of the reference hydrocarbon-bearing substance is produced, wherein distinguishable characteristic signals with respective second times are designated. Two distinguishable characteristic signals and their respective first and second times are selected from the above-described analyses and a linear relationship for offset between the two analyses is derived therefrom. Contemporaneously with the second analysis of the reference hydrocarbon-bearing substance, an analysis of a first sample hydrocarbon-beraing substance having an unknown specific composition is produced, wherein distinguishable characteristic signals with respective times are designated. All times of the distinguishable characteristic signals produced in the analysis of the first sample hydrocarbon-bearing substance are shifted by the linear relationship determined between the two reference analyses. A determination is made of whether the time of a distinguishable characteristic signal of the sample analysis shifted by the linear relationship is within a preselected tolerance of a first time of a distinguishable characteristic signal designated in the first reference hydrocarbon-bearing substance analysis and if so, further shifting the time of any such signal until it is at substantially the same time as the corresponding signal designated in the first reference hydrocarbon-bearing substance analysis. Contemporaneously with the second analysis of the reference hydrocarbon-bearing substance, an analysis of a second sample hydrocarbon-bearing substance having an unknown specific composition is produced in the same manner as for the first sample hydrocarbon-bearing substance. The time-shifted distinguishable characteristic signals of the first sample hydrocarbon-bearing substance analysis are compared with the time-shifted distinguishable characteristic signals of the second sample hydrocarbon-bearing substance analysis.

The present invention also provides a method of reservoir analysis for one or more subterranean fluid-containing reservoirs. A first well fluid sample is extracted from a well drilled into the earth; a second well fluid sample is extracted from a well drilled into the earth. At a first time, a reference substance is analyzed in equipment to identify characteristics at respective times. At a second time, the reference substance is analyzed in equipment to identify characteristics at respective times. Data from the reference substance analyses are input into a computer. A time offset relationship is derived in the computer between a selected pair of characteristics from the analysis at a first time of the reference substance and a selected pair of corresponding characteristics from the analysis at a second time of the reference substance. Contemporaneously with the second time, the first well fluid sample is analyzed in equipment to identify at respective times characteristics of the first well fluid sample. Contemporaneously with the second time, the second well fluid sample is analyzed in equipment to identify at respective times characteristics of the second well fluid sample. Data from analyses of the first and second well fluid samples are input into the computer. In the computer, characteristics of the first well fluid sample analysis are compared relative to corresponding characteristics of the analysis at a first time, of the reference substance as follows: Associated respective times of the first well fluid sample analysis are changed by the time offset relationship established between the two analyses of the reference substance; changed associated respective times of the first well fluid sample analysis are compared with times of the analysis, at first time, of the reference substance and a fine adjusted time offset relationship is determined therebetween; and changed associated respective times of the first well fluid sample analysis are further changed in response to the fine adjustment time offset relationship. In the computer, characteristics of a second well fluid sample analysis are compared relative to corresponding characteristics of the analysis, at a first time, of the reference substance as follows: Associated respective times of the second well fluid sample analysis are changed by the time offset relationship established between the two analyses of the reference substance; changed associated respective times of the second well fluid sample analysis are compared with times of the analysis, at a first time, of the reference substance and a fine adjusted time offset relationship ·is determined therebetween; and changed associated respective times of the second well fluid sample analysis are further changed in response to the fine adjustment time offset relationship. Correlated characteristics pertaining to the first well fluid sample are compared with correlated characteristics pertaining to the second well fluid sample to determine whether the two well fluid samples have common or different characteristics to thereby suggest whether the first and second well fluids communicate with a common reservoir or different reservoirs.

The present invention also provides a method of aligning sample records so that the aligned sample records define a database on which a meaningful statistical analysis can be performed, wherein the sample records are gas chromatography/mass spectrometry (GC/MS) peak-time records for a plurality of samples. In this method, a primary standard GC/MS peak-time record for a selected reference substance is defined; for each group of one or more of the sample records created contemporaneously with the same equipment, a respective secondary standard GC/MS peak-time record for the selected reference substance is defined; for each secondary standard record, a relationship as to time offset between the primary standard record and the respective secondary standard record is determined; for each of the one or more sample records of each group, times associated with peaks thereof are adjusted by the relationship determined for the respective secondary standard record of the respective group so that each sample record of the respective group is coarsely adjusted to the primary standard record; and for each coarsely adjusted sample record, peaks thereof are finely adjusted to corresponding peaks of the primary standard record wherein each such peak of the respective sample record is associated with the same time as the respective corresponding peak of the primary standard record so that all the sample records are aligned to the primary standard record and thereby to each other for providing a database of aligned sample records subject to meaningful statistical analysis.

The present invention is particularly suitable for, but not limited to, facilitating the interpretation of GC/MS data. This has particular utility in the oil and gas industry where unknown substances taken from wells are processed through GC/MS equipment. A particular advantage of the present invention is its capability of aligning diverse records to a common standard.

DETAILED DESCRIPTION OF THE PREFERRED EMBODIMENTS

Figure 1:
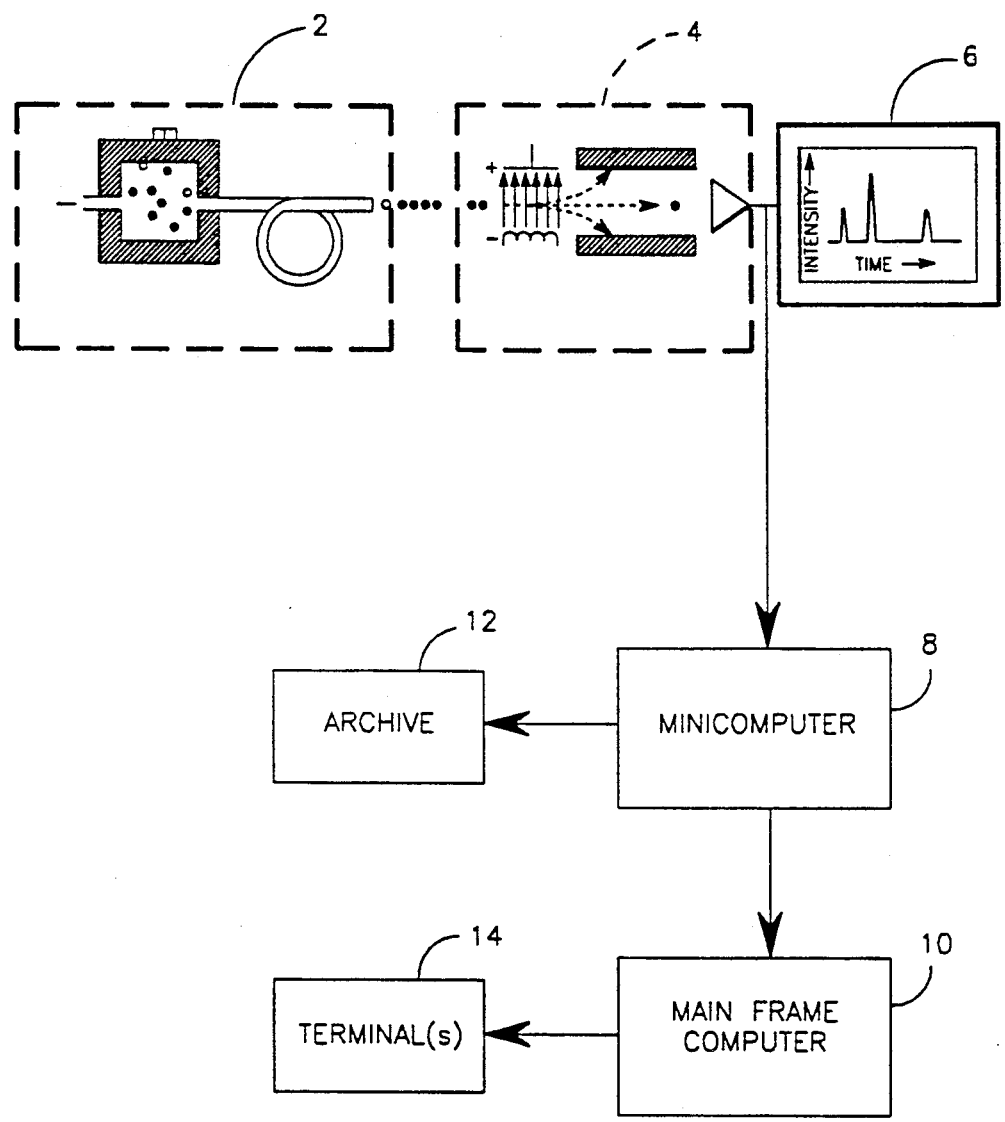
FIG. 1 is a schematic and block diagram of equipment with which the present invention can be performed.

The present invention provides a method of aligning a time record of sample data (e.g., a mass chromatogram of an unknown sample substance) with a time record of reference data (e.g., a mass chromatogram of a known reference substance). This includes producing a coarse time-related alignment between the sample data and the reference data. This coarse time alignment is done independently of any similarities and differences between the sample data and the reference data. The method further includes determining which, if any, distinguishing coarsely aligned sample data (e.g., peaks of the sample mass chromatogram) are within a predetermined time-related tolerance of any distinguishing reference data (e.g., peaks of the reference mass chromatogram). For each distinguishing sample data which is within a predetermined time-related tolerance of a respective distinguishing reference data, the method further includes producing a fine time-related alignment between the respective sample data and its respective reference data so that the respective sample data is then recorded with substantially the same time designation as the respective reference data. As used herein, "substantially the same time" includes both exactly the same time and any small deviations resulting therefrom of a type as would be known to those skilled in the art or as could be inherent in an actual implementation.

The present invention has particular application in time-aligning the signals of mass chromatograms or ion chromatograms (which terms when generally referred to herein can be used interchangeably). An example of where chromatograms can be used is the oil and gas industry. In this industry mass chromatograms or ion chromatograms are used in analyzing unknown hydrocarbon-bearing substances and in analyzing subterranean fluid-containing reservoirs. The present invention, however, has broader utility, such as in time aligning sample records of any suitable type so that the time-aligned sample records define a database on which a meaningful statistical analysis can be performed.

Regardless of the particular application to which the present invention is put, the present invention broadly includes coarsely aligning the sample data to the reference data regardless of similarities or differences between the sample data and the reference data, and then finely aligning distinguishable sample data to distinguishable reference data. The coarse alignment is performed by using a primary standard and a secondary standard, both pertaining to the same reference so that an offset relationship can be determined between the two. This offset relationship is then applied to coarsely align the sample data to the primary standard. Thereafter, fine alignment is performed. This fine alignment can be by any suitable known technique or otherwise.

Referring now to the drawings, the present invention will be more fully described.

The invention will be described with reference to the alignment of data obtained through a combination of gas chromatography and mass spectrometry. The invention facilitates the qualitative and quantitative interpretation of this data which can be useful, for example, in classifying or categorizing oil samples.

Figure 4:
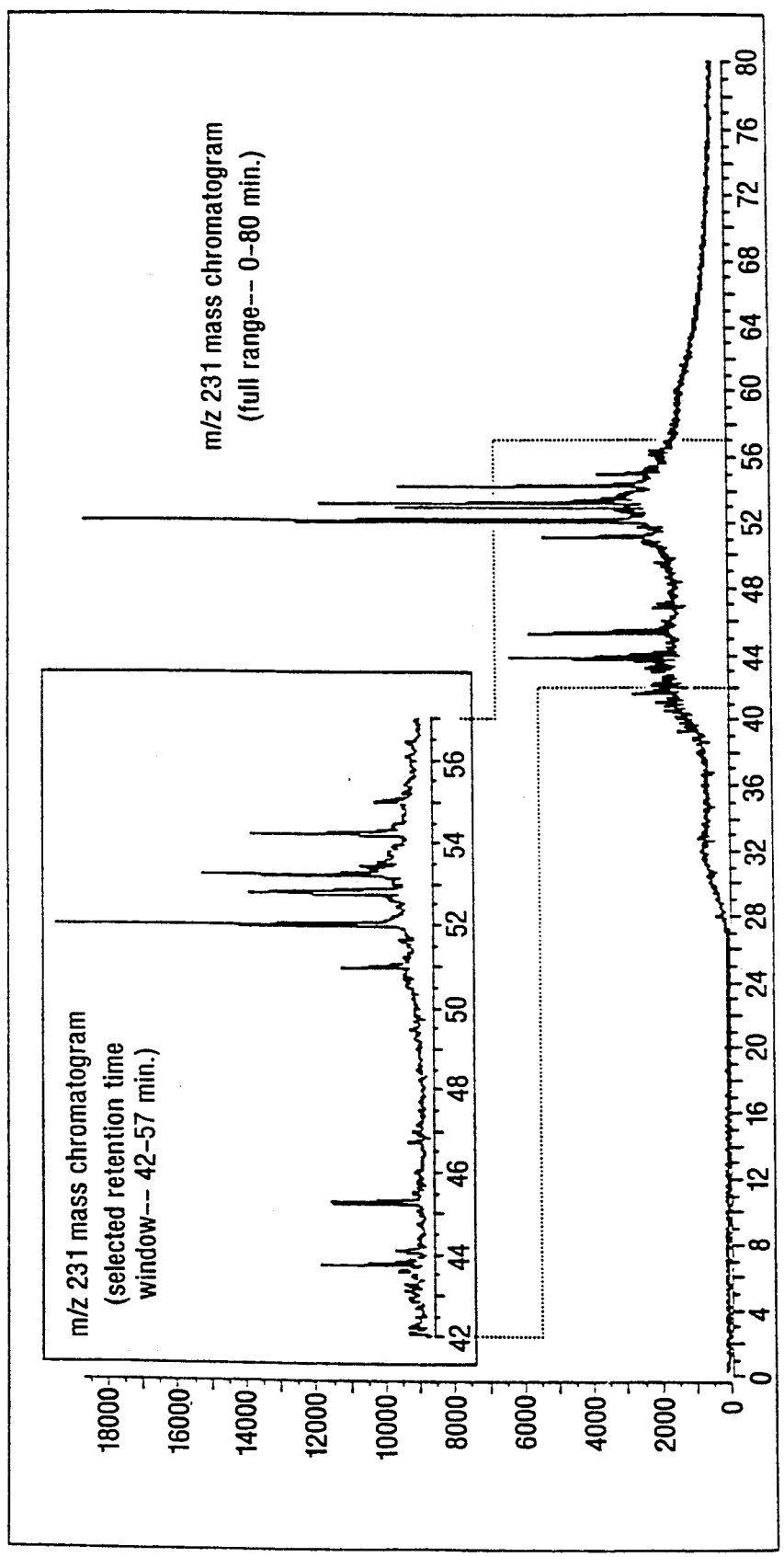
FIG. 4 is an example of a primary standard mass chromatogram of a reference substance, showing an enlargement of a window of interest.

A schematic representation of conventional gas chromatography (GC) and mass spectrometry (MS) equipment is illustrated in FIG. 1. The GC equipment is identified by the reference numeral 2 and the MS equipment is identified by the reference numeral 4. A mass chromatogram 6 provides a visual representation of ion intensity or abundance data versus time as known to the art. An example of a mass chromatogram for m/z 231 (characterizing a class of compounds called triaromatic steranes) is shown in FIG. 4 with the characteristic "fingerprint" or window-of-interest shown in the inset. This chromatogram shows distinguishable peak signals representing detected ion intensities or abundance versus retention time (in subsequent ones of the drawings, time designations by scan numbers are also shown--the scan number is the integer number of the order the abundance/intensity value was taken). For a given substance, such as an oil sample, a number of chromatograms 6 are produced, one for each of the designated detected ions found in the substance.

The chromatogram data produced by the GC/MS equipment is also collected, in encoded digital form, by a computer 8, such as a Hewlett-Packard minicomputer programmed in a conventional way known to the art for collecting these data. The data are stored within the computer system 8, such as on a disk, for eventual transfer to a mainframe computer 10. The data can also be transferred from the computer 8 to a conventional archive 12, such as magnetic tape.

The mainframe computer 10 can be any suitable computer, such as an IBM 370 computer operating under the VM operating system. Coarse alignment and fine alignment application procedures used within this environment are those which align the individual sample mass chromatograms to primary standard mass chromatograms which have been previously obtained and stored in the computer 10. The information contained in the computer 10 can be put in a formal database providing an inventory of data available to be accessed by a set of criteria input by users through one or more terminals 14 connected in known manner to the computer 10. Data retention within the computer 10 can be by any suitable means. Because of the quantity of information which might need to be processed, increased storage such as is provided by an optical disk might be useful.

Under the coarse alignment and fine alignment application procedures (which will be more fully described herein-below), a user can align GC/MS data either automatically or manually (interactively). The purpose of the alignment is to assure that distinguishing characteristics, namely the intensity peak apexes, of a given sample mass chromatogram occur at the same scan position or retention time as do corresponding distinguishing characteristics of the primary standard.

The basic system just described can be expanded by adding additional application procedures to a master selection menu. All application procedures should operate on aligned GC/MS data thus making quantitative comparisons possible. For example, one application procedure might calculate correlation coefficients between aligned GC/MS samples and generate a report of the results.

All procedures are resident on the mainframe computer 10 due to the memory, storage and performance requirements needed to manipulate the volume of GC/MS data. A particular configuration of this system calls for a virtual machine to have four megabytes of memory and an A-disk storage capacity of 20 cylinders or more (actual disk storage capacity is dependent upon the number and size of sample data files required for a particular project).

The procedures of interest with respect to the present invention are those which perform the coarse alignment and fine alignment functions. Flow charts for the coarse alignment and fine alignment procedures are shown in FIGS. 2A-2C and 3, respectively. These will be described in detail after first giving an overview of an example of the present invention applied to the alignment of mass chromatograms.

Overview

Broadly, the present invention relates to the combination of coarse and fine alignment described herein; however, there must first be data which are to be aligned.

Periodically, such as each week, a standard or reference sample (LCU-150 lab standard crude oil in the pertinent chromatograms shown in FIGS. 4-11) is run in the laboratory as a check on the performance of the GC/MS system 2, 4. Mass chromatograms from these analyses serve as calibration curves for the alignment process of the present invention.

Figure 5:
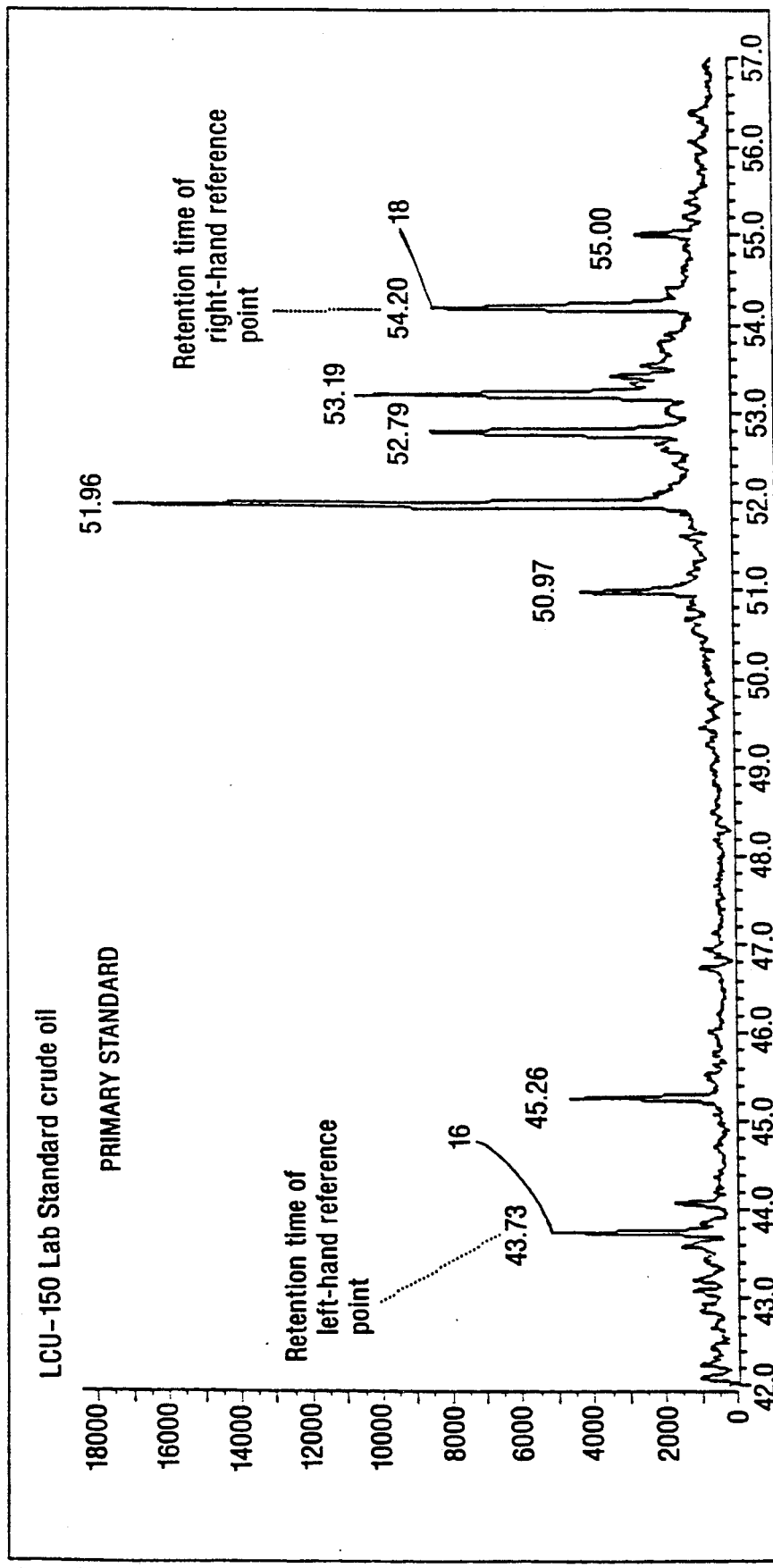
FIG. 5 is an enlargement showing the window of interest of the primary standard mass chromatogram with peaks labeled with retention times.

One of the LCU-150 runs is chosen as the "primary standard" to which all other runs are to be referenced. The choice of the primary standard is arbitrary, but the primary standard is fixed once the choice is made. The mass chromatogram shown in FIGS. 4 (full range) and 5 (window of interest) is the primary standard used for illustrative purposes in the present description of the invention. The window-of-interest endpoints shown in FIG. 5 (42.0 and 57.0) are preselected as being appropriate to obtain a suitable "fingerprint" for the particular ion. Two peak apexes (referred to hereinafter simply as "peaks") near the extremes of the window of interest shown in FIG. 5 are chosen as reference points. These peaks are identified by the reference numerals 16, 18, respectively, in FIG. 5. The retention times of the reference peaks for the primary standard are recorded in a primary standard endpoint file.

Figure 6:
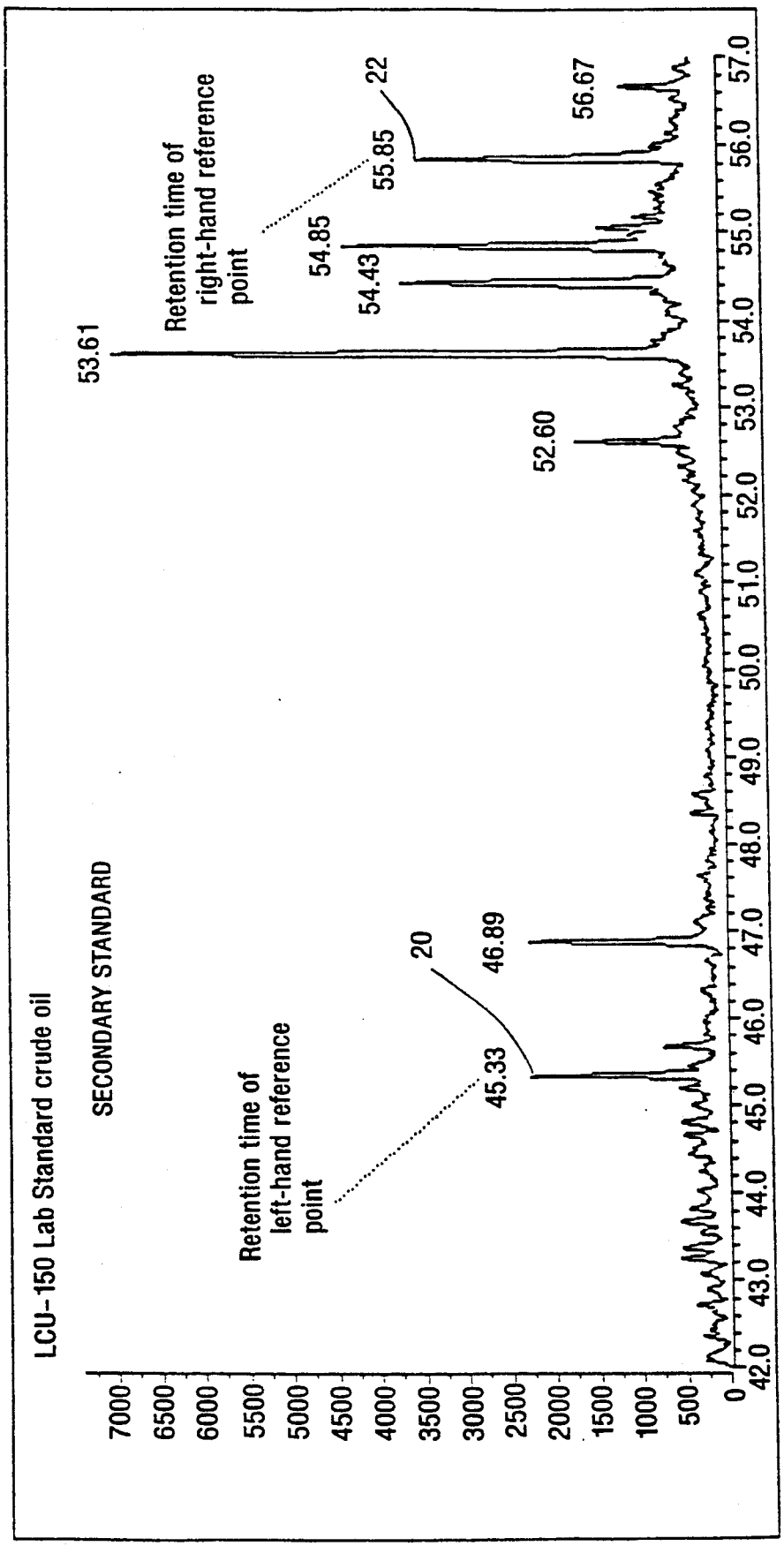
FIG. 6 shows the portion of a secondary standard ion chromatogram for the same time segment selected as the window of interest of the primary standard mass chromatogram.

Next, an LCU-150 standard run in the GC/MS equipment the same week as one or more unknown samples of interest is picked as a secondary standard. An example of a portion of a secondary standard is shown in FIG. 6. The same two peaks as selected in the primary standard are identified in the secondary standard (these peaks are identified by the reference numerals 20, 22 corresponding to the peaks 16, 18, respectively). The retention times of the peaks 20, 22 are entered into the computer in a secondary standard endpoint file.

Figure 7:
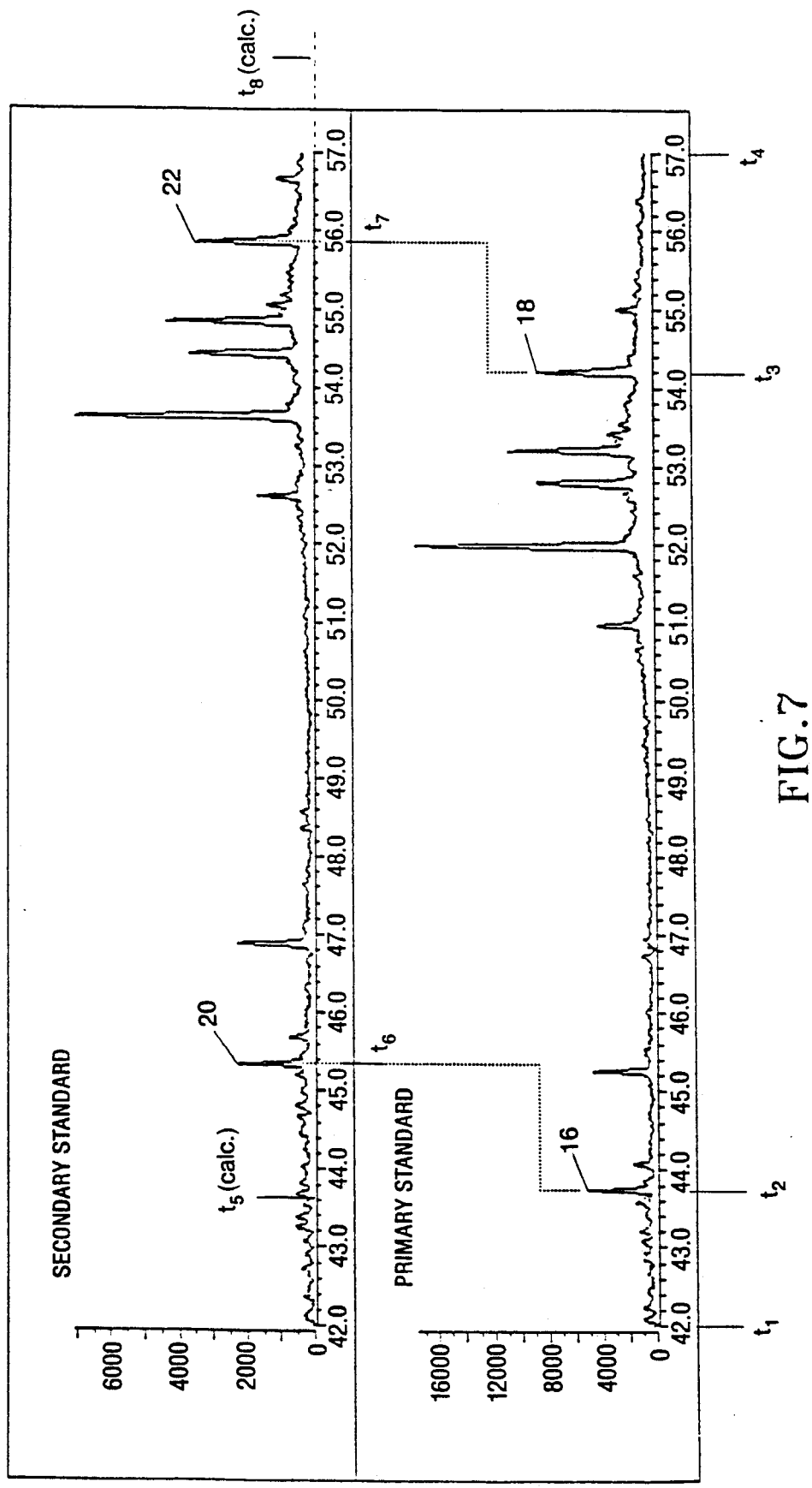
FIG. 7 is a comparison of the primary standard mass chromatogram and the secondary standard mass chromatogram showing offset between selected corresponding peaks.
Figure 8:
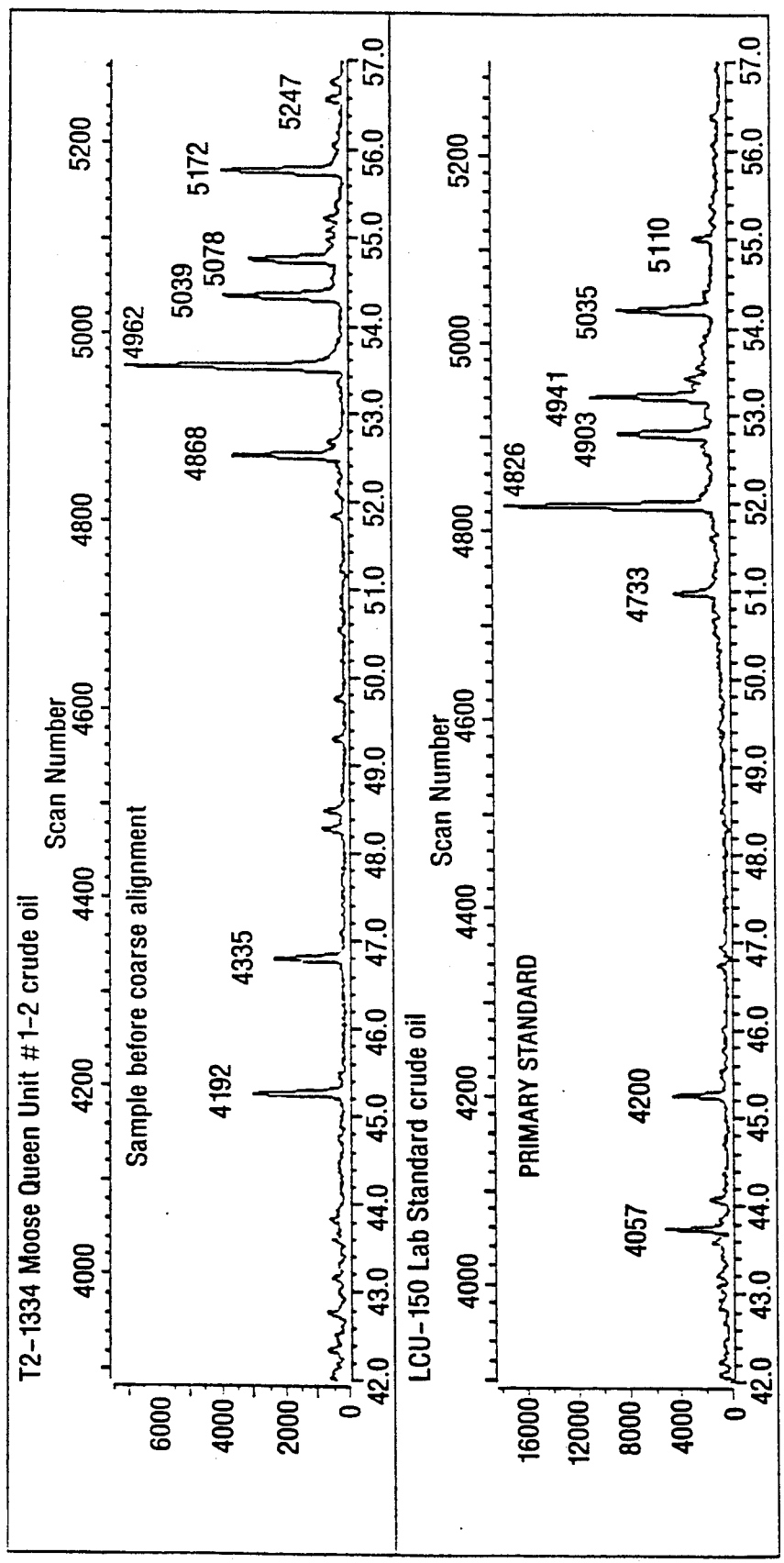
FIG. 8 shows the same time sections of a sample ion chromatogram and the primary standard mass chromatogram before coarse alignment of the sample mass chromatogram by the present invention.

Referring to FIG. 7, it will be noted that despite the primary and secondary standards both being made in response to the same reference substance, the retention times at which the peaks are designated are different. This can result from flow changes, procedure temperature variations, column aging, etc. When the two offset chromatograms are of the same ion, it is easy to see the time shift and to correct for it because it is known that the peaks of both mass chromatograms represent the same things. This is not the case, however, for a mass chromatogram of a sample substance. Then it is not necessarily apparent merely from a visual inspection whether there is simply non-alignment or whether the sample chromatogram identifies something different at properly different times. It is a purpose of the present invention to align a sample chromatogram with a known primary standard chromatogram so that a determination can be made as to whether the sample chromatogram identifies the same thing identified in the primary standard. It is another purpose of the present invention to enable multiple sample chromatograms to be aligned to the same primary standard so that they can be directly compared with each other.

Because of the time offset between the primary standard and secondary standard, their aforementioned endpoint files are used to define a relationship which in turn is used to determine endpoints of the secondary standard which are defined as corresponding to the endpoints of the window of interest of the primary standard. The preselected endpoints of the primary standard and the determined endpoints of the secondary standard are then used to define a relationship which is used to shift the retention times of peaks and other signals in respective portions of one or more sample mass chromatograms for other samples run during the same time period (i.e., within the same week for our specific example) as the secondary standard. This produces a coarse alignment between a sample chromatogram and the primary standard chromatogram. From this coarse alignment, an adjusted peak of the sample chromatogram within a predetermined tolerance of a peak of the primary standard chromatogram is finely aligned so that it is designated by substantially the same retention time (or scan number) as the corresponding peak of primary standard. Thus, all sample chromatograms for a given ion are aligned to the same scale as the primary standard for that ion.

At subsequent times, such as each succeeding week, a new secondary standard is produced and a relationship with the same primary standard is derived to coarsely align the signals of associated mass chromatograms for samples tested during that period to those of the primary standard. This relationship is applied to all samples of interest run during that time period (e.g., that week) whereby peaks of the sample mass chromatograms are coarsely aligned to corresponding peaks of the primary standard. Fine alignment then occurs in the same manner as described above. This procedure gives mass chromatograms which are all aligned with the single, common primary standard and which are, therefore, aligned to each other.

This procedure can be performed for each class of compounds which may be within sample substances. Thus, each week (or other selected time) additional standards of marker compounds for only a few compounds may be needed when an analysis of particular types of substances are to be made. Possible marker compounds for the analysis of hydrocarbon fluids extracted from oil or gas wells include steranes, triaromatic steroid hydrocarbons, hopanes, paraffins, aromatics, etc.

Obtaining Data for Alignment

From the foregoing overview, it is apparent that the combination of coarse and fine alignment according to the invention is implemented using records of data. A specific important utility of this invention is within the context of a method of reservoir analysis for one or more subterranean fluid-containing reservoirs. This analysis is to be achieved by comparing at least two sample hydrocarbon-bearing substances, from which one might determine whether the substances come from the same or different reservoirs or source rocks. This is particularly implemented by analyzing a sample substance using mass chromatograms in which constituents of substances are designated by signals aligned to time designations. The present invention is used to align signals of a sample chromatogram to signals within a time window of a primary standard chromatogram using a secondary standard chromatogram, which primary and secondary chromatograms are made in response to a reference hydrocarbon-bearing substance.

In the foregoing context, fluid samples are extracted from wells drilled into the earth. These samples are analyzed in equipment to identify at respective times characteristics of the samples from the wells. Specifically, these samples are processed through the GC/MS equipment depicted in FIG. 1 so that mass chromatograms are obtained. Each of these mass chromatograms includes peaks which define a particular type of distinguishable characteristic signal of the analysis. These analyses are made contemporaneously with (such as within a week of) the making of a secondary standard mass chromatogram.

In obtaining a secondary standard chromatogram, the reference hydrocarbon-bearing substance is processed through the GC/MS equipment to produce distinguishable characteristic signals in the form of peaks of a mass chromatogram. Prior to the secondary standard having been obtained, the primary standard is obtained by analyzing the reference substance to designate distinguishable characteristic signals in the form of peaks of an mass chromatogram. It is to be noted that only a single primary standard is always maintained, but a plurality of secondary standards and sample chromatograms can be processed over time. By maintaining a single primary standard, however, all the sample chromatograms are aligned to the common standard and thus to each other. This allows for direct comparisons between the adjusted sample chromatograms.

Once a primary standard chromatogram has been produced and selected, a time window, or window of interest, is selected. This is the portion for which an alignment is to be made. A time window is defined by two time endpoints such as the 42.0-minute and 57.0-minute endpoints shown in FIG. 5. Two distinguishing signals at two times within the time window of the primary standard are also selected. For our illustrated example, these would be the peak 16 at retention time 43.73 and peak 18 at retention time 54.20 shown in FIG. 5. For an automatic mode of operation, the selection of the endpoints and reference peaks of the primary standard has been predetermined by one who has set up the system. That is, the window of interest and reference peaks for a particular primary standard are whatever is deemed suitable by the user (such as based upon his or her experience or some standard definition for a "fingerprint" of a known ion). Once selected, however, these are maintained.

It is contemplated that the automatic alignment which proceeds from the preselected endpoints and reference peaks of the GC/MS data of the primary standard works well with most of the data to be aligned. Some sample chromatograms are, however, too complex to be aligned automatically. For these, a manual alignment capability is required. This would proceed with one viewing the peak versus time graphic image of the primary standard chromatogram on a display connected to the mainframe computer, and entering into the computer two times from the graphic image for defining endpoints of the time window. Likewise, two signals, one at one time and the other at another time within the time window, would be selected. These signals would preferably be apexes of peaks of the graphic image near the endpoints of the time window. These would be retained in the computer. The corresponding peaks of the secondary standard chromatogram would likewise be manually selected.

Regardless of whether automatic or manual alignment is used, the signal data and the retention time data of each of the chromatograms is ultimately stored in the mainframe computer 10. Each chromatogram's signal data, representing the ion accumulation information including the peaks, is retained in one file and the corresponding retention times are retained in another file. Entries within the files are in the order in which they were derived in the GC/MS equipment so their positions are designated by "scan numbers."

With these data entered in the mainframe computer 10, the coarse alignment and fine alignment procedures are applied to produce the desired alignments. The coarse alignment procedure will be described with reference to the flow chart shown in FIGS. 2A-2C and the chromatograms depicted in FIGS. 4-9. Thereafter the fine alignment procedure will be described with reference to the flow chart shown in FIG. 3 and the chromatograms shown in FIGS. 10 and 11.

Coarse Alignment

Broadly, the coarse alignment procedure produces, independently of any similarities and differences between the sample data and the reference data, a coarse time-related alignment between the sample data and the reference data. With reference to our example using chromatograms, this produces a coarse time-related sample mass chromatogram. The preferred embodiment of the present invention implements this by the procedure shown in FIGS. 2A-2C. This will be described with reference to the primary standard of FIG. 5, the secondary standard of FIG. 6 and the sample chromatogram shown beginning in FIG. 8.

Figure 2A:
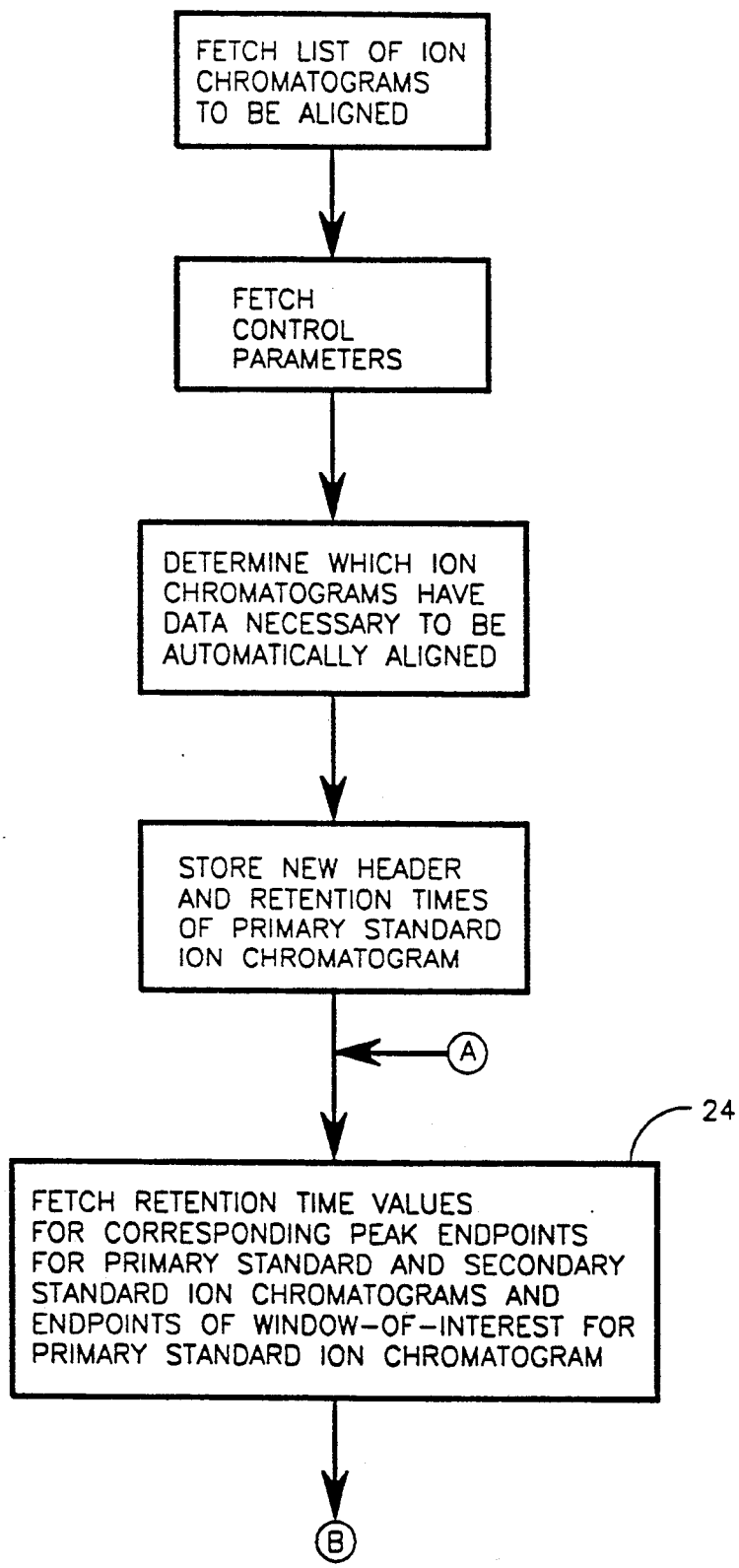
FIGS. 2A-2C form a flow chart of a procedure for a coarse alignment portion of the present invention.

Referring to the first function of FIG. 2A, a list of mass chromatograms to be aligned is fetched or entered in the mainframe computer 10. That is, a list of individual ions whose chromatograms are to be aligned to respective primary standards is defined. Each sample substance after being analyzed through the GC/MS equipment of FIG. 1 likely has a plurality of chromatograms related to different compounds contained within the sample. These are obtained by programming the GC/MS equipment to monitor for selected ions. This produces, as described hereinabove, a number of chromatograms, each relating to one of the selected ions if the ion is present in the sample. There is a corresponding primary standard and one or more secondary standards for each ion. These are preferably obtained prior to the sample chromatograms in a similar manner as described above.

The next function identified in FIG. 2A is to fetch control parameters. These relate to selecting between automatic or manual alignment, for example.

The coarse alignment procedure next determines which ion chromatograms have the data necessary to be automatically aligned if automatic alignment is to occur. At this point, the procedure determines whether there is a primary standard for each of the ions identified to be aligned.

The next function identified in FIG. 2A ("store new header . . . ") pertains to additional setup information.

At point "A" in FIG. 2A, there begins the loop wherein a mass chromatogram is coarsely aligned each time through the loop. This loop broadly includes determining a relationship between signals of the primary and secondary standards and then adjusting, by this relationship, signals of the mass chromatogram of the sample substance. In the preferred embodiment shown in FIGS. 2A-2C, the relationship is determined by functions 24-32, and the adjustment is made by functions 34-38.

By function 24, the retention time values for the two corresponding peak endpoints of the primary and secondary standards are fetched, as are the preselected endpoints of the window of interest of the primary standard. With reference to FIGS. 5-7, the retention times for the pair of distinguishable characteristic signals identified as the pair of peaks 16, 18 and for the pair of distinguishable characteristic signals identified a the pair of peaks 20, 22 are fetched. Along with these, the preselected window of interest time endpoints of 42.0 minutes and 57.0 minutes are also fetched. These six retention times are used to commence the determination of the time offset relationship between the primary and secondary standards, which offset is apparent in FIG. 7. This relationship is then used for adjusting all sample chromatograms obtained contemporaneously with the respective secondary standard ("contemporaneously" means within whatever time period is selected as ideally representing stable GC/MS operation, e.g., one week in our overview example).

Figure 2B:
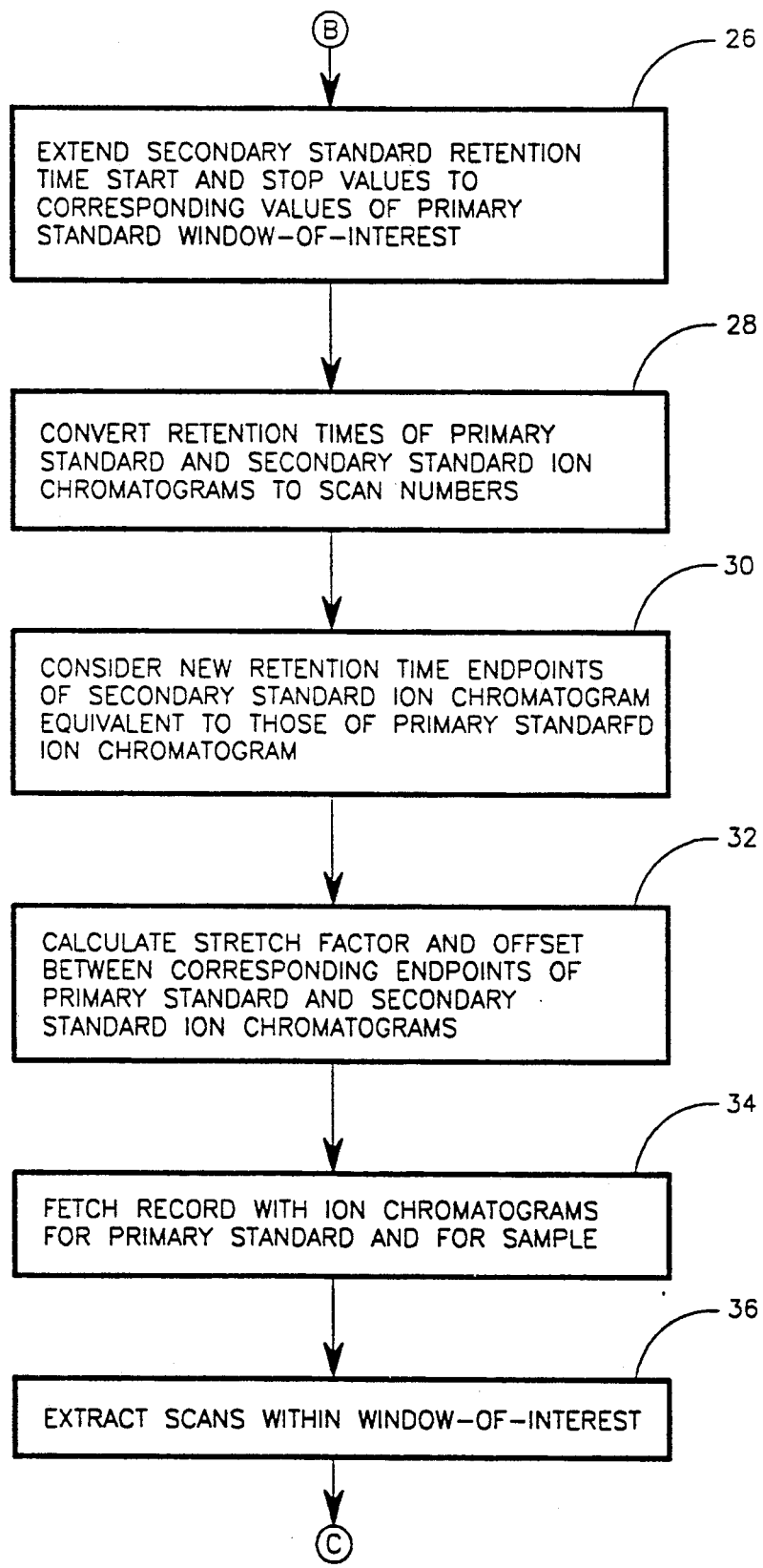

Referring to FIG. 2B, function 28 is self-explanatory, but functions 26 and 30 include the following general steps: (1) computing a ratio between the time differentials of two selected reference data from two different time records of the reference data, wherein one of the two different time records is the primary standard to which the time record of sample data is to be aligned and wherein the other of the two different time records is the secondary standard; (2) computing a first endpoint time differential between the preselected first endpoint (window-of-interest endpoint) of the primary standard and a first one of the two selected reference data of the secondary standard, multiplying the first endpoint time differential by the ratio, and subtracting the product from the corresponding first one of the two selected reference data of the secondary standard to define a first endpoint of the secondary standard; (3) computing a second endpoint time differential between the preselected second endpoint of the primary standard and a second one of the two selected reference data of the secondary standard, multiplying the second endpoint time differential by the ratio, and adding the product to the corresponding second one of the two selected reference data of the secondary standard to define a second endpoint of the secondary standard.

Referring to the example of FIGS. 4-11, step (1) includes computing the ratio between the length of time between the peaks 16, 18 of the primary standard and the length of time between the corresponding peaks 20, 22 of the secondary standard. Referring to FIG. 7, this ratio is $$\frac{t_7 - t_6}{t_3 - t_2}$$

From the specific times shown in FIGS. 5 and 6, this ratio equals in this example $$\frac{55.85 - 45.33}{54.20 - 43.73} = 1.005$$

Step (2) includes multiplying the ratio by the length of time between the primary standard's left-hand endpoint at $t_1 = 42.0$ and its peak 16 at $t_2 = 43.73$. This defines a product which is subtracted from the retention time $t_6 = 45.33$ of the corresponding peak 20 of the secondary standard to define the left-hand endpoint, $t_5$, of the secondary standard. Thus, $$t_5 = t_6 - \left[ (t_2 - t_1) \frac{t_7 - t_6}{t_3 - t_2} \right] =$$

$$45.33 - (43.73 - 42.0)(1.005) = 43.59$$

Step (3) includes multiplying the ratio by the length of time between the primary standard's peak 18 at $t_3 = 54.20$ and its right-hand endpoint $t_4 = 57.0$. This product is added to the time $t_7 = 55.85$ of the peak 22 of the secondary standard to define the right-hand endpoint, $t_8$, of the secondary standard. Thus, $$t_8 = t_7 + \left[ (t_4 - t_3) \frac{t_7 - t_6}{t_3 - t_2} \right] = 55.85 +$$

$$(57.0 - 54.20)(1.005) = 58.66$$

The preselected endpoints of the primary standard and the computed endpoints of the secondary standard are used in calculating the stretch factor and offset factor called for in function 32. The stretch factor and offset define the relationship between the signals of the primary and secondary standards. In the preferred embodiment, this relationship is a linear one determined as follows: $t_1 = mt_5 + b$ and $t_4 = mt_8 + b$, solving for m (the stretch factor) and b (the offset). For our specific example:

$$42.0 = m(43.61) + b \quad 57.0 = m(58.66) + b; \text{ therefore,}$$

$$m = 0.998 \text{ and } b = -1.523.$$

Figure 9:
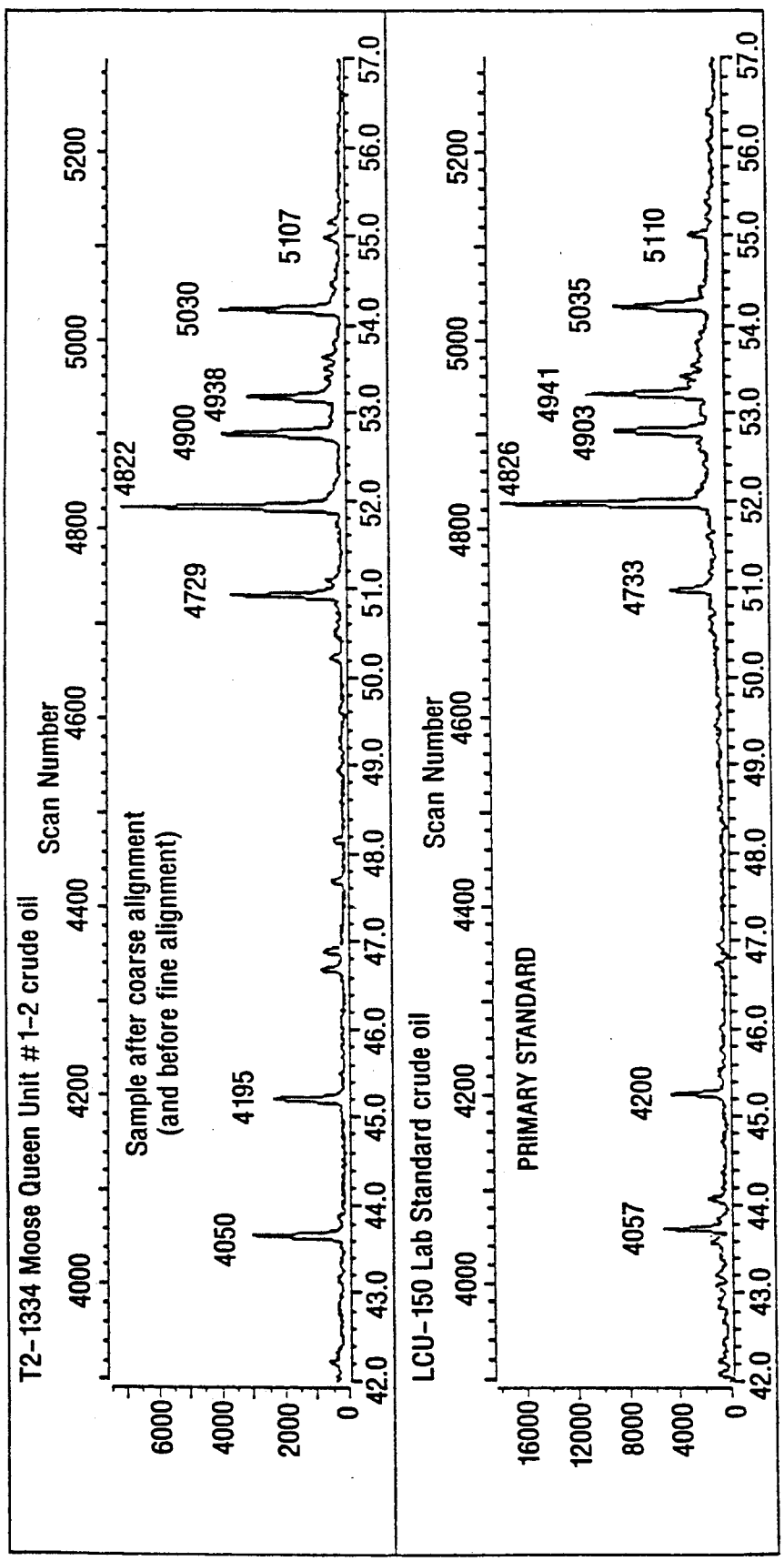
FIG. 9 shows the respective portions of the sample and primary standard mass chromatograms shown in FIG. 8, but after the sample mass chromatogram has been coarsely aligned in accordance with the present invention.
Figure 10:
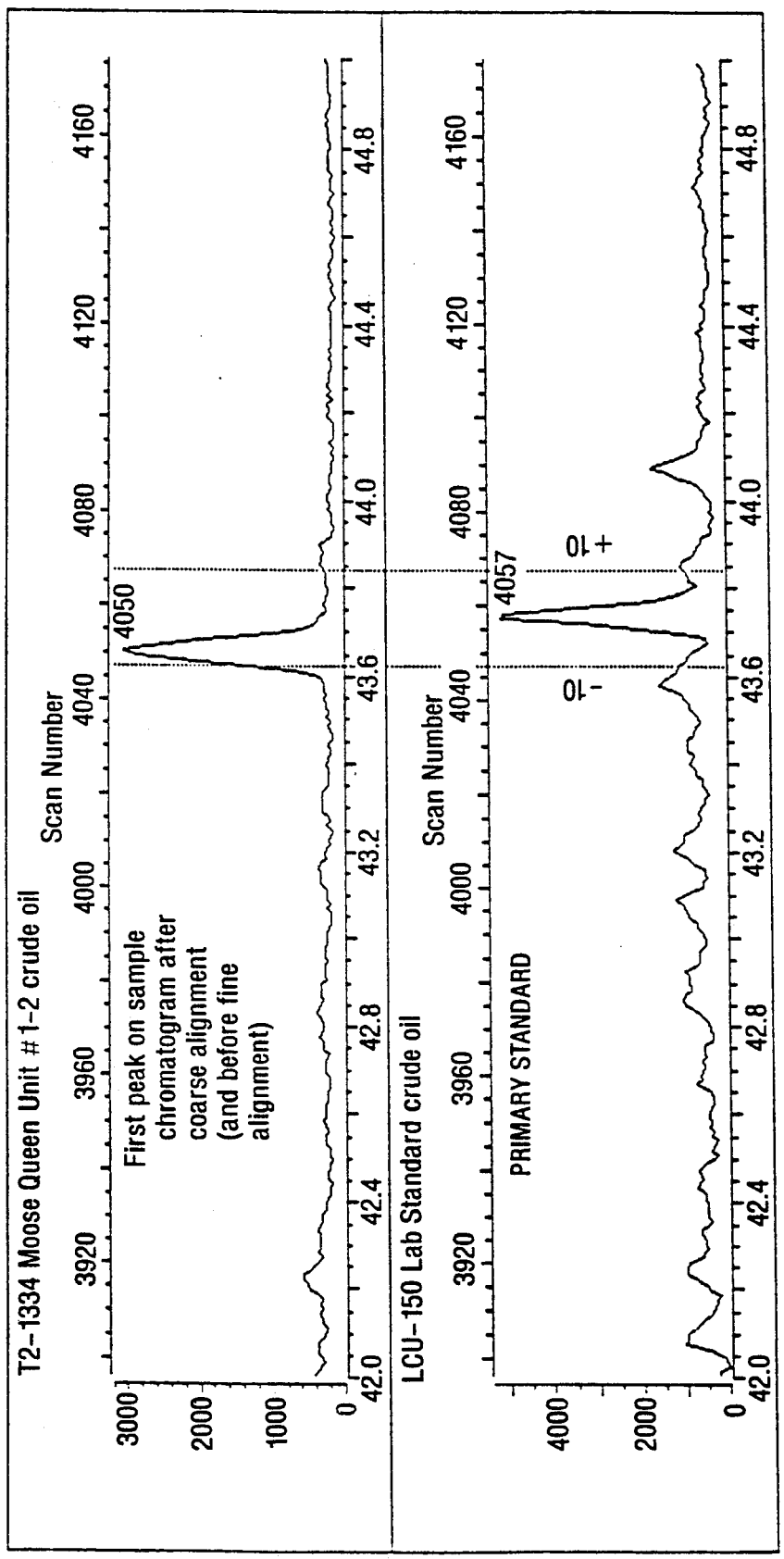
FIG. 10 shows the same time sections of the sample and primary standard mass chromatograms containing the first corresponding peaks shown in FIG. 9 after coarse alignment but before fine alignment by the present invention.

Once the stretch factor and offset have been determined, the procedure shown in FIG. 2B proceeds to the function 34. Functions 34 and 36 simply bring up a respective mass chromatogram in the portion thereof to be adjusted. By function 38 recited in FIG. 2C, the retention times in the file for a respective chromatogram are adjusted using the following equation: $t_a = m \cdot t_i + b$ where $t_i$ is a respective initial retention time contained in the file and $t_a$ is the respective adjusted time which is calculated and stored in place of the respective $t_i$. Thus, each of the retention times within the pertinent portion of the sample chromatogram are adjusted. The coarsely adjusted sample chromatogram for our specific example is shown in FIG. 9.

Figure 2C:
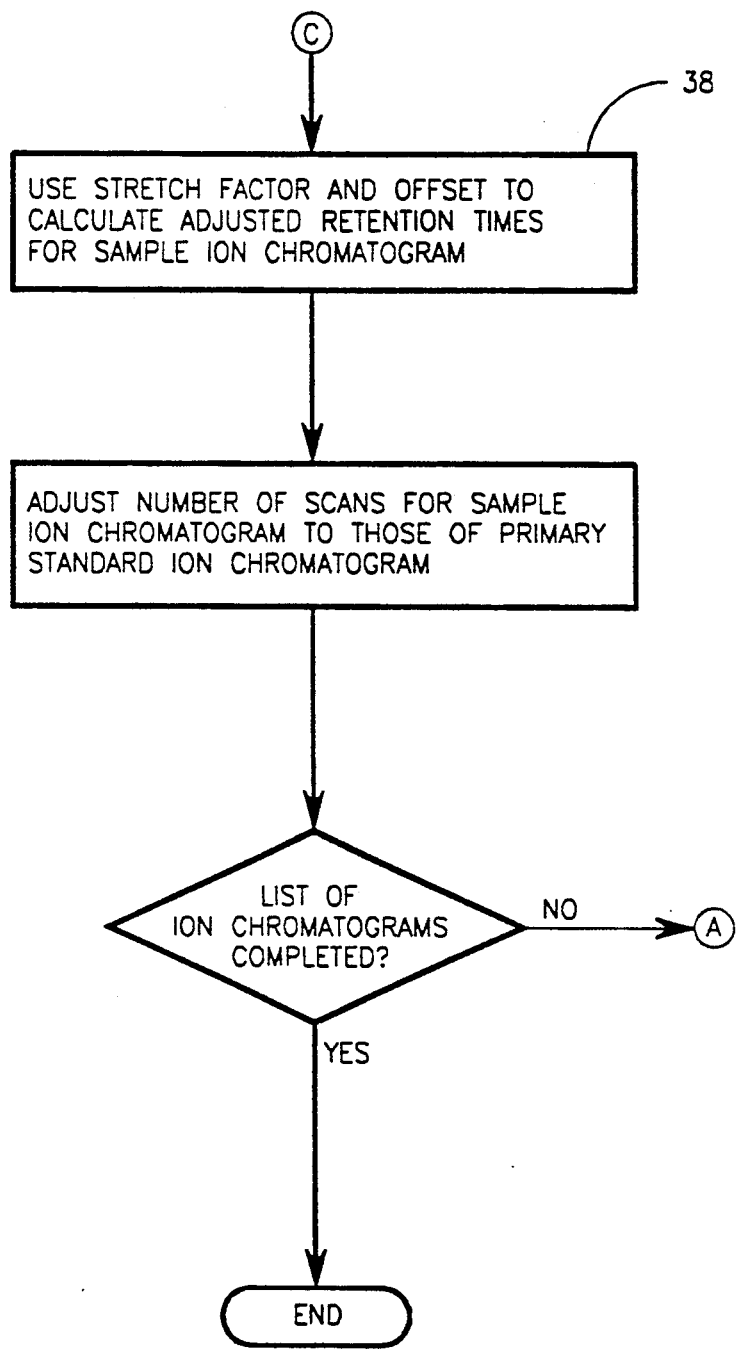

The procedure shown in FIG. 2C continues to the next function of adjusting the number of scans for a sample chromatogram to those of the primary standard. This is done by spline interpolation routines available, for example, from the International Mathematical and Statistical Libraries (IMSL). Specific routines include ICSCCU, ICSEVU, CSAKM and CSVAL. Spline interpolation equalizes the number of data points within the sample chromatogram and the primary standard chromatogram within the window of interest. From this, a point difference between the sample chromatogram and the primary standard chromatogram for each curve segment can serve as an indicator of those areas of the sample chromatogram where problems might have occurred during alignment. The point differences are, in the preferred embodiment, shown in a bar graph above the final aligned curves (not shown). Areas having large numbers of data points added or deleted over a relatively short horizontal distance indicate possible problem areas.

The coarse alignment procedure continues by looping until all the mass chromatograms have been adjusted. By performing the coarse alignment, the times of peaks in the sample mass chromatograms which should correspond to peaks in the primary standard should be shifted within a few seconds (or scan numbers) of their corresponding peaks in the primary standard. This is sufficiently close for the final alignment routine which can use previously known techniques for producing the final alignment on a direct peak-by-peak basis between the sample chromatogram and the primary standard chromatogram.

It is to be noted that the coarse alignment routine can be performed using scan numbers or retention times. Retention times have been used in the preferred embodiment because it has been discovered that the number of scans within a window is not necessarily constant from sample to sample due to variable data acquisition times. That is, more time is required to collect and process data within a region of strong response than in a region of low or no response. This problem is overcome by converting all data to retention times. Thus, in the preferred embodiment it is contemplated that the use of retention times produces a closer, more reliable alignment.

It is to be further noted that the present invention contemplates the use of other techniques for achieving the coarse alignment. For example, a linear relationship could be obtained by using the reference peaks 16, 18 and 20, 22 as the points from which the stretch factor m and the offset b are determined. It is contemplated that other relationships could be utilized and remain within the scope of the present invention, which broadly pertains to first producing a coarse alignment and then a fine alignment to obtain a body of commonly aligned samples which can be directly compared to each other regardless of any initial apparent differences between the samples and a common primary standard.

Fine Alignment

The fine alignment procedure broadly includes determining which, if any, distinguishing coarsely aligned sample data (i.e., peaks of the sample chromatograms in our example) are within a predetermined time-related tolerance of any distinguishing reference data (i.e., peaks of the primary standard in our example); and, for each distinguishing sample data which is within a predetermined time-related tolerance of a respective distinguishing reference data, producing a fine time-related alignment between the respective sample data and its respective reference data so that the respective sample data is then recorded with substantially the same time designation as the respective reference data. The predetermined time-related tolerance is in the preferred embodiment a range on either side of a selected peak. More preferably this is measured as ±scan numbers from the scan number of the peak, but retention times could also be used. In the preferred embodiment this produces an adjusted sample mass chromatogram wherein a peak of the sample chromatogram which corresponds to a peak of the primary standard is designated in the adjusted mass chromatogram by substantially the same time designation as that of the corresponding signal of the primary standard.

Figure 3:
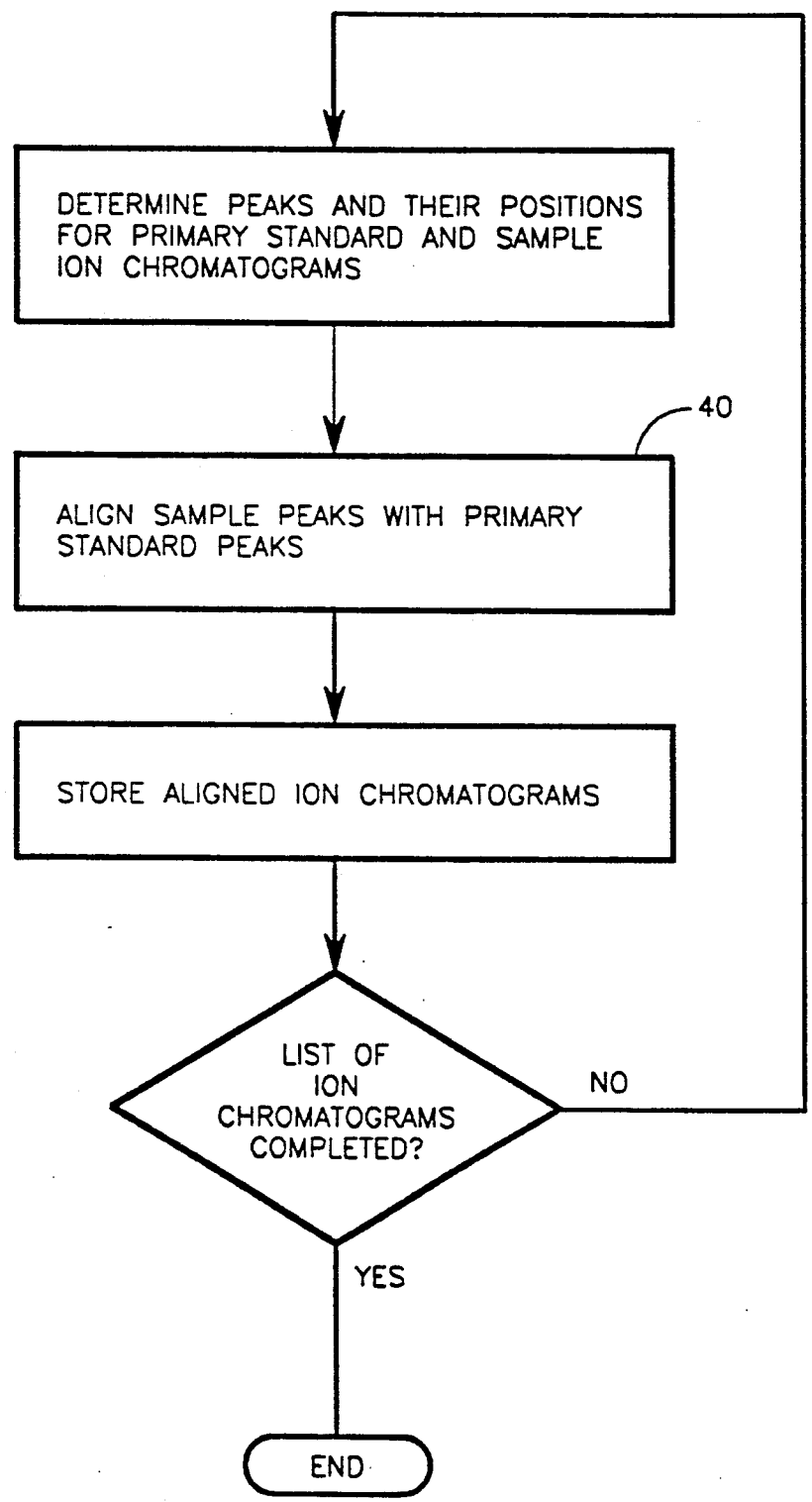
FIG. 3 is a flow chart of a procedure for a fine alignment portion of the present invention.
Figure 11:
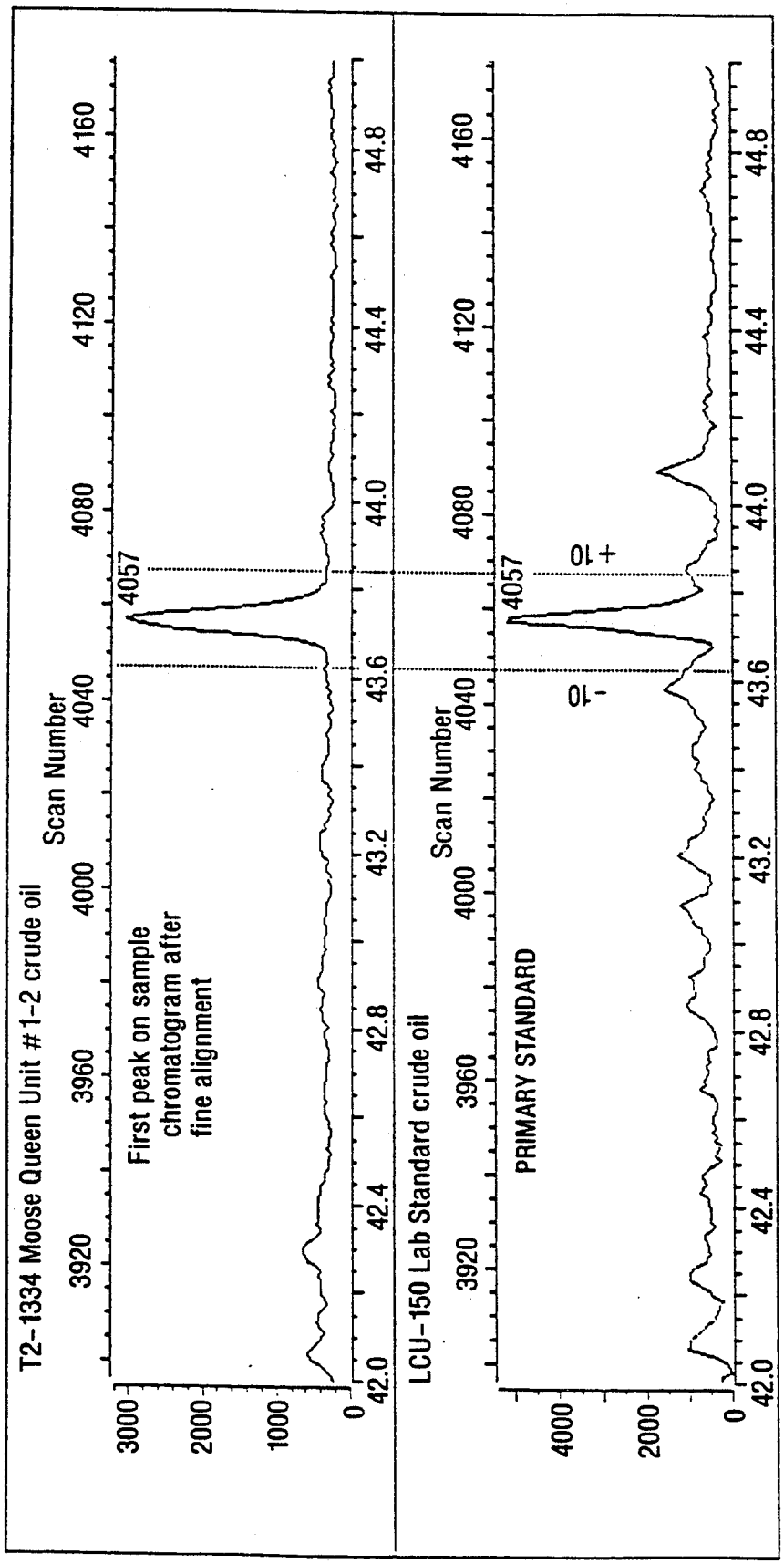
FIG. 11 shows the sections shown in FIG. 10 but after the peak of the sample mass chromatogram has been finely aligned with the corresponding peak of the primary standard mass chromatogram in accordance with the present invention.

More specifically with reference to our example, the first step in the fine alignment procedure is to determine the peak positions, using scan numbers of the peak apexes, in both the primary standard and sample chromatograms. For each peak in the primary standard chromatogram, a search is made in the sample chromatogram for a corresponding peak. If a peak in the sample chromatogram occurs within ten scan numbers on either side of a peak in the primary standard chromatogram, it is considered a match (see FIG. 10). The peak apex in the sample chromatogram is shifted to match that of the primary standard as shown in FIG. 11. The sample chromatogram is then compressed or expanded, using spline interpolation of the same type as performed during the coarse alignment procedure, to insure the same number of scans in the sample chromatogram as in the primary standard chromatogram between adjacent identified peaks. This compression-expansion procedure is repeated for all peaks. The flow chart for this procedure is shown in FIG. 3.

The fine alignment procedure can be implemented by known procedures in that there are known procedures which can "pick peaks" out of a collection of digitally stored data. There are also procedures which can align one peak relative to another when the former is within a certain tolerance of the latter. In the preferred embodiment of the present invention, however, a routine similar to that used in the coarse alignment is used. This is done in the function 40 identified in FIG. 3 after a conventional "peak picker" procedure has determined the peaks and their positions.

In function 40, each peak apex position in the primary standard chromatogram is compared to each peak apex in the sample chromatogram. All the sample peaks which are within a given scan tolerance of those in the primary standard are collected in an array. When sample peaks are separated by less than the given scan tolerance of a peak of the primary standard, these peaks are flagged as one peak. It is determined whether one or two peaks exist within the same scan tolerance in the sample chromatogram. If one peak is present, it is paired to the closest primary standard chromatogram peak within the tolerance. If two sample peaks are present, the left one is paired with the left one of the primary standard and the right is paired with the right of the primary standard if two peaks are within the scan tolerance of the primary standard. Using the scan numbers defining the locations of an adjacent pair of peaks of the sample chromatogram and their corresponding peaks of the primary standard, a stretch factor and offset are calculated using the linear equations described hereinabove for computing m and b. The stretch factor and offset are then used to calculate new retention times of the signals of the sample chromatogram within that range of the adjacent peaks. This is then repeated for all the sections of pairs of peaks. Spline interpolation is performed and the foregoing procedure can be repeated using a smaller scan tolerance.

The foregoing describes the routine which is followed when there are not more peaks in the sample chromatogram than are in the primary standard. If there are more peaks in the sample chromatogram, then the foregoing routine is used but the sample peaks are used as guides for the pairing of peaks rather than the primary standard peaks; however, the sample peaks are still aligned to the position values of the primary standard peaks.

The foregoing invention can be repeated for multiple sample chromatograms relative to a single primary standard. It can also be applied to multiple sample chromatograms for different ions with respect to a number of respective primary standard chromatograms. It can also be implemented over time so that multiple secondary standards are used, each of which has been contemporaneously produced with a respective group of one or more sample chromatograms; this could include: defining a primary standard GC/MS peak-time record for a selected reference substance; for each group of one or more of the sample records created contemporaneously with the same equipment, defining a respective secondary standard GC/MS peak-time record for the selected reference substance; for each secondary standard record, determining a relationship as to time offset between the primary standard record and the respective secondary standard record; for each of the one or more sample records of each group, adjusting times associated with peaks thereof by the relationship determined for the respective secondary standard record of the respective group so that each sample record of the respective group is coarsely adjusted to the primary standard record; and for each coarsely adjusted sample record, finely adjusting peaks thereof to corresponding peaks of the primary standard record wherein each such peak of the respective sample record is associated with the same time as the respective corresponding peak of the primary standard record so that all the sample records are aligned to the primary standard record and thereby to each other for providing a database of aligned sample records subject to meaningful statistical analysis.

When multiple sample chromatograms are aligned to a common primary standard, this allows a direct comparison of the time-shifted distinguishable characteristic signals of each of the analyses of various substances with the time-shifted distinguishable characteristic signals of other analyses of substances. Thus, with respect to our example of analyzing hydrocarbon-bearing substances, chromatograms pertaining to the same ion but obtained from different sample substances can be compared to determine similarities and differences between the substances. This is useful in determining whether the samples have common or different constituents to thereby suggest whether they came from wells communicating with a common reservoir or different reservoirs or came from the same or different source rocks. More generally, use of the present invention produces a database of aligned sample records subject to meaningful statistical analysis.

The invention described above can be automatically implemented so that the coarse and fine alignments occur automatically. It is contemplated that automatic alignment can be done with most data. Some sample chromatograms, however, may be too complex to be aligned automatically. These can be handled by manual alignment incorporating the foregoing features but also providing for interactive capability by a user working at the terminal 14. In such case, instead of the procedure automatically identifying peaks for alignment, the user chooses which peaks of the sample chromatogram correspond to which peaks of the primary standard chromatogram. The procedure then uses the same alignment process employed by the automatic procedure to align the chromatograms. The process can be repeated as many times as needed to obtain the desired alignment. A combination of automatic and manual alignment can even be used. Typically, automatic alignment would be done, followed by the user changing the result as desired before the aligned curves are filed.

Situations may arise in which a sample produces an ion chromatogram that does not appear in the primary or secondary standards. Provisions can be made to add mass chromatograms to the primary standard to give a composite standard to which all subsequent mass chromatograms can be aligned. There are occasions when a given ion of the primary standard chromatogram does not have a peak (or peaks) at a certain location to represent a particular compound (or group of compounds). Such peaks can be added to the primary standard from other samples which have the same ion displaying a distinctive peak pattern for the compounds of interest. The source curve for the appropriate mass chromatogram would be chosen and the peak or peaks from the curve to be added to the primary standard chromatogram would be specified by two endpoints. That portion of the curve would be spliced into the primary standard. An additional feature allows for the scaling of the peak height as a percentage of the maximum abundance of the primary standard.

While presently preferred embodiments of the invention have been described herein for the purpose of disclosure, numerous changes in the construction and arrangement of parts and the performance of steps will suggest themselves to those skilled in the art, which changes are encompassed within the spirit of this invention as defined by the appended claims.

What is claimed is:

1. A method of comparing at least two unknown hydrocarbon-bearing substances, comprising the steps of:
   (a) producing a first analysis of a reference hydrocarbon-bearing substance, including processing the reference hydrocarbon-bearing substance in gas chromatography/mass spectrometry equipment for obtaining a first mass chromatogram therefrom and designating distinguishable characteristic signals of the first mass chromatogram with respective first time;
   (b) producing a second analysis of the reference hydrocarbon-bearing substance, including processing the reference hydrocarbon-bearing substance in gas chromatography/mass spectrometry equipment for obtaining a second mass chromatogram therefrom and designating distinguishable characteristic signals of the second mass chromatogram with respective second times;
   (c) selecting from the analyses of said steps (a) and (b) two distinguishable characteristic signals and their respective first and second times and deriving therefrom a linear relationship for offset between the analyses of said steps (a) and (b);
   (d) producing, contemporaneously with said step (b), an analysis of the first sample hydrocarbon-bearing substance having an unknown specific composition, including processing the first sample hydrocarbon-bearing substance in gas chromatography/mass spectrometry equipment for obtaining a third mass chromatogram therefrom and designating distinguishable characteristic signals with respective times;
   (e) shifting times of the distinguishable characteristic signals produced in said step (d) by the linear relationship determined in said step (c);
   (f) determining whether the time of a distinguishable characteristic signal shifted in said step (e) is within a preselected tolerance of a first time of a distinguishable characteristic signal designated in said step (a) and if so, further shifting the time of any such signal shifted in said step (e) until it is at substantially the same time as the corresponding signal designated in said step (a);
   (g) repeating said steps (d) through (f) for a second sample hydrocarbon-bearing substance having an unknown specific composition including processing the second sample hydrocarbon-bearing substance in gas chromatography/mass spectrometry equipment for obtaining a fourth mass chromatogram therefrom; and
   (h) comparing the time-shifted distinguishable characteristic signals of the first sample hydrocarbon-bearing substance analysis as shifted in said step (f) with the time-shifted distinguishable characteristic signals of the second sample hydrocarbon-bearing substance analysis as shifted in said step (g).

2. A method as defined in claim 1, further comprising inputting data from the four mass chromatograms into a digital computer and performing said steps (c), (e), (f) and (h) with the computer.

3. A method as defined in claim 1, wherein said step (c) includes:
   computing a ratio between a first length of time between the two distinguishable characteristic signals of the analysis of said step (a) and a second length of time between the two corresponding signals of the analysis of said step (b);
   multiplying the ratio by a third length of time between a first endpoint of the analysis of said step (a) and a first one of the two distinguishable characteristic signals of the analysis of said step (a) to define a first product;
   multiplying the ratio by a fourth length of time between a second one of the two distinguishable characteristic signals of the analysis of said step (a) and a second endpoint of the analysis of said step (a) to define a second product;
   subtracting the first product from the first one of the corresponding two signals of the analysis of said step (b) to define a first endpoint of the analysis of said step (b);
   adding the second product to the second one of the corresponding two signals of the analysis of said step (b) to define a second endpoint of the analysis of said step (b); and
   computing a stretch factor and an offset between the corresponding first and second endpoints of the analyses wherein the stretch factor and offset define the linear relationship.

4. A method of reservoir analysis for at least one subterranean fluid-containing reservoir, comprising the steps of:
   (a) extracting a first well fluid sample from a well drilled into the earth;
   (b) extracting a second well fluid sample from a well drilled into the earth;
   (c) analyzing, at a first time, a reference substance in equipment to identify characteristics at respective times, including processing the reference substance in gas chromatography/mass spectrometry equipment and obtaining a first mass chromatogram therefrom;
   (d) analyzing, at a second time, the reference substance in equipment to identify characteristics at respective times, including processing the reference substance in gas chromatography/mass spectrometry equipment and obtaining a second mass chromatogram therefrom;
   (e) inputting data from said steps (c) and (d) into a computer;
   (f) deriving, in the computer and from a selected pair of characteristics from said step (c) and from a selected pair of corresponding characteristics from said step (d), a time offset relationship between the analyses made in said steps (c) and (d);
   (d) analyzing, contemporaneously with the second time, the first well fluid sample in equipment to identify at respective times characteristics of the first well fluid sample including processing the first well fluid sample in gas chromatography/mass spectrometry equipment and obtaining a third mass chromatogram therefrom (h) analyzing, contemporaneously with the second time, the second well fluid sample in equipment to identify at respective times characteristics of the second well fluid sample including processing the second well fluid sample in gas chromatography/-mass spectrometry equipment and obtaining a fourth mass chromatogram therefrom (i) inputting data from said steps (g) and (h) into the computer;

(j) comparing, in the computer, characteristics of said step (g) relative to corresponding characteristics of said step (c), said step (j) including:

(j1) changing associated respective times of said step (g) by the time offset relationship of said step (f);

(j2) comparing changed associated respective times of said step (j1) with times of said step (c) and determining a fine adjusted time offset relationship therebetween; and (j3) further changing changed associated respective times of said step (j1) in response to the fine adjustment time offset of said step (j2);

(k) comparing, in the computer, characteristics of said step (h) relative to corresponding characteristics of said step (c), said step (k) including:

(k1) changing associated respective times of said step (h) by the time offset relationship of said step (f);

(k2) comparing changed associated respective times of said step (k1) with times of said step (c) and determining a fine adjusted time offset relationship therebetween; and (k3) further changing changed associated respective times of said step (k1) in response to the fine adjustment time offset of said step (k2); and (l) comparing aligned characteristics of said step (j) pertaining to the first well fluid sample with aligned characteristics of said step (k) pertaining to the second well fluid sample to determine whether the two well fluid samples have common or different characteristics to thereby suggest whether the first and second well fluids communicate with a common reservoir or different reservoirs.

5. A method as defined in claim 4, wherein said step (f) includes:

computing a ratio between a first length of time between the members of the pair of characteristics and a second length of time between the members of the pair of corresponding characteristics;

multiplying the ratio by a third length of time between a first endpoint of the analysis of said step (c) and a first member of the pair of characteristics to define a first product;

multiplying the ratio by a fourth length of time between a second member of the pair of characteristics and a second endpoint of the analysis of said step (c) to define a second product;

subtracting the first product from the corresponding first member of the pair of corresponding characteristics to define a first endpoint of the analysis of said step (d);

adding the second product to the corresponding second member of the pair of corresponding characteristics to define a second endpoint of the analysis of said step (d); and computing a linear relationship between the corresponding first and second endpoints of the analyses of said step (c) and (d) to define the time offset relationship.

* * * * *

UNITED STATES PATENT AND TRADEMARK OFFICE
CERTIFICATE OF CORRECTION

PATENT NO.  : 5,119,315
DATED       : June 2, 1992
INVENTOR(S) : Marwin K. Kemp, et al It is certified that error appears in the above-indentified patent and that said Letters Patent is hereby corrected as shown below:

Col. 3, line 29, "hydrocarbon-beraing" should read
--hydrocarbon-bearing--.

Col. 17, line 26, "first time;" should read --first times--.

Signed and Sealed this

Twenty-eighth Day of September, 1993

Attest:

BRUCE LEHMAN

*Attesting Officer*      *Commissioner of Patents and Trademarks*